(12) United States Patent
Nagao et al.

(10) Patent No.: US 8,915,937 B2
(45) Date of Patent: Dec. 23, 2014

(54) PUNCTURE NEEDLE CARTRIDGE

(71) Applicant: Panasonic Corporation, Osaka (JP)

(72) Inventors: Akio Nagao, Kagawa (JP); Kouji Miyata, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 13/938,625

(22) Filed: Jul. 10, 2013

(65) Prior Publication Data

US 2013/0331879 A1   Dec. 12, 2013

Related U.S. Application Data

(63) Continuation of application No. 13/122,830, filed as application No. PCT/JP2009/005300 on Oct. 9, 2009.

(30) Foreign Application Priority Data

Oct. 9, 2008 (JP) .................................. 2008-262981

(51) Int. Cl.
*A61B 17/32* (2006.01)
*A61B 5/151* (2006.01)
*A61B 5/15* (2006.01)

(52) U.S. Cl.
CPC ............ *A61B 5/1513* (2013.01); *A61B 5/15113* (2013.01); *A61B 5/150282* (2013.01); *A61B 5/150549* (2013.01); *A61B 5/150717* (2013.01); *A61B 5/150916* (2013.01); *A61B 5/15186* (2013.01); *A61B 5/150412* (2013.01); *A61B 5/1519* (2013.01); *A61B 5/150267* (2013.01); *A61B 5/150022* (2013.01); *A61B 5/150618* (2013.01); *A61B 5/1411* (2013.01); *A61B 5/15117* (2013.01)
USPC ......................................... 606/181

(58) Field of Classification Search
USPC ........... 606/167, 170, 181–183, 185; 600/583
See application file for complete search history.

(56) References Cited

U.S. PATENT DOCUMENTS 5,318,584 A    6/1994   Lange et al.
5,741,288 A *  4/1998   Rife .............................. 606/181

(Continued)

FOREIGN PATENT DOCUMENTS

JP    2000-245717    9/2000
JP    2004-290390    10/2004

(Continued)

OTHER PUBLICATIONS

International Search Report issued Dec. 8, 2009 in International (PCT) Application No. PCT/JP2009/005300.

(Continued)

*Primary Examiner* — Ryan Severson
(74) *Attorney, Agent, or Firm* — Wenderoth, Lind & Ponack, LLP

(57) ABSTRACT

A puncture needle cartridge including a puncture needle, a lancet body adapted to cover part or all of a tip of the puncture needle, a cylindrical puncture needle holder disposed on an outer surface of the lancet body to permit the lancet body to move in an axial direction of the puncture needle; and a protective cap that is separable from the puncture needle holder. The protective cap includes a base adapted to cover an opening in the puncture needle holder, a shaft protruding from the base, and arms mounted on the shaft and configured to abut an inner circumferential surface of the opening in the puncture needle holder by spreading in the opening. A space between tips of the arms is larger than an inside diameter of the opening in the puncture needle holder, and is reduced by elastic deformation when the arms are housed in the opening.

6 Claims, 22 Drawing Sheets

(56) References Cited

U.S. PATENT DOCUMENTS

2002/0103499 A1  8/2002  Perez et al.
2006/0129172 A1  6/2006  Crossman et al.
2006/0253146 A1  11/2006  Marshall et al.

FOREIGN PATENT DOCUMENTS

| JP | 3115405 | 9/2005 |
|---|---|---|
| JP | 2006-520231 | 9/2006 |
| JP | 3134339 | 7/2007 |
| WO | 2006/118224 | 11/2006 |
| WO | 2008/041437 | 4/2008 |

OTHER PUBLICATIONS

International Preliminary Report on Patentability issued Jun. 16, 2011 in International (PCT) Application No. PCT/JP2009/005300.

* cited by examiner

PUNCTURE NEEDLE CARTRIDGE

This application is a continuation of Ser. No. 13/122,830, now U.S. Pat. No. 8,506,587, which is the national stage of International Application No. PCT/JP2009/005300 filed Oct. 9, 2009.

BACKGROUND OF THE INVENTION

I. Technical Field

The present invention relates to a puncture needle cartridge for a puncture device used to take blood for blood measurements such as blood sugar measurements.

II. Description of the Related Art

Various puncture devices used to take blood as well as disposable lancets used therewith have been developed conventionally. With such a puncture device, there is a danger that a user may accidentally prick his/her finger on a puncture needle exposed from one end of the lancet when mounting and dismounting the lancet to/from the puncture device. In view of the above problem, puncture needle cartridges have been developed which comprise a cap adapted to enclose the puncture needle, eliminate the danger of touching the puncture needle directly, and allow the lancet to be attached and detached to/from the puncture device (see, for example, Japanese Patent Laid-Open No. 2000-245717 and International Publication No. WO 2006/118224).

Such a puncture needle cartridge comprises a lancet body and a protective cap separable from the lancet body, where the lancet body comprises a puncture needle on one end and a chucking unit on the other end. The chucking unit is used to chuck the puncture needle cartridge to the puncture device. Each puncture needle cartridge is attached to the puncture device for use and detached after use. Before puncture, protective cap is twisted off from the lancet body.

SUMMARY OF INVENTION

Such a conventional puncture needle cartridge is used for puncture after twisting off the protective cap from the lancet body. However if the puncture needle cartridge is recapped with the protective cap (the protective cap is returned to the puncture needle cartridge) after puncture or disposal, it is difficult to determine whether the puncture needle cartridge is a used item or an unused item. Consequently, there is a possibility that a used needle will be reused by mistake. If a used needle is reused by mistake, there is a problem, i.e., there is a danger of infection accidents.

The present invention has been made in view of the above problem and has an object to provide a puncture needle cartridge which can prevent a used lancet from being reused due to difficulty to determine whether a puncture needle cartridge is a used item or an unused item if recapped with a protective cap after puncture.

A puncture needle cartridge according to the present invention comprises: a puncture needle adapted to puncture skin; a lancet body adapted to cover and protect part or all of a tip of the puncture needle; a puncture needle holder configured to be cylindrical, placed on an outer circumferential surface of the lancet body so as to allow the lancet body to move in an axial direction of the puncture needle, and provided with an opening through which the puncture needle is allowed to protrude; and a protective cap adapted to cover and protect the opening and configured to be separable from the puncture needle holder, wherein the protective cap comprises a base adapted to cover the opening when the protective cap is joined to the puncture needle holder and a pair of raised walls which protrude from the base toward the puncture needle holder and whose tip portions are placed facing each other, the tip portions of the raised walls pinch the puncture needle holder when the protective cap is joined to the puncture needle holder, and after the protective cap is separated from the puncture needle holder, a space between the tip portions of the raised walls becomes smaller than an outside diameter of the puncture needle holder.

A puncture needle cartridge according to the present invention comprises: a puncture needle adapted to puncture skin; a lancet body adapted to cover and protect part or all of a tip of the puncture needle; a puncture needle holder configured to be cylindrical, placed on an outer circumferential surface of the lancet body so as to allow the lancet body to move in an axial direction of the puncture needle, and provided with an opening through which the puncture needle is allowed to protrude; and a protective cap adapted to cover and protect the opening and configured to be separable from the puncture needle holder, wherein the protective cap comprises a base adapted to cover the opening when the protective cap is joined to the puncture needle holder, a shaft protruding from the base toward the opening, and arms mounted on the shaft and adapted to abut an inner circumferential surface of the opening in the puncture needle holder by spreading in the opening, and space between tips of the arms is larger than an inside diameter of the opening in the puncture needle holder, and is reduced by elastic deformation when the arms are housed in the opening.

A puncture needle cartridge according to the present invention comprises: a puncture needle adapted to puncture skin; a lancet body adapted to cover and protect part or all of a tip of the puncture needle; a puncture needle holder configured to be cylindrical, placed on an outer circumferential surface of the lancet body so as to allow the lancet body to move in an axial direction of the puncture needle, and provided with an opening through which the puncture needle is allowed to protrude; and a protective cap adapted to cover and protect the opening and configured to be separable from the puncture needle holder, wherein the puncture needle holder comprises a first engaging part formed on an inner circumferential surface of the opening, the protective cap comprises a base adapted to cover the opening when joined, a shaft protruding from the base toward the opening, and a second engaging part formed on an outer circumferential surface of the shaft and adapted to engage with the first engaging part, and the first engaging part and the second engaging part separably engage with each other by elastic deformation in response to an action tending to separate the protective cap from the lancet body and comprise respective jagged surfaces adapted to disable engagement in response to a recapping action tending to attach the protective cap to the lancet body.

A puncture device according to the present invention is adapted to puncture skin using a needle and comprises a puncture button used to puncture the skin with a needle, wherein any of the above-described puncture needle cartridges according to the present invention provided with a recapping prevention function is detachably attached to the puncture device, and the puncture device punctures the skin using the attached puncture needle cartridge when the puncture button is pressed.

According to the present invention, the inclined portions of the protective cap prevent recapping by engaging with an end portion of the puncture needle holder, making it possible to prevent a used lancet from being reused due to difficulty to determine whether a puncture needle cartridge is a used item or an unused item if recapped with a protective cap after puncture. Therefore, this prevents a patient from recapping the puncture needle cartridge which has been used for puncture with the protective cap and thereby prevents infection accidents.

DETAILED DESCRIPTION OF THE INVENTION

Embodiments of the present invention will be described in detail below with reference to the drawings.
(First Embodiment)

Figure 1:
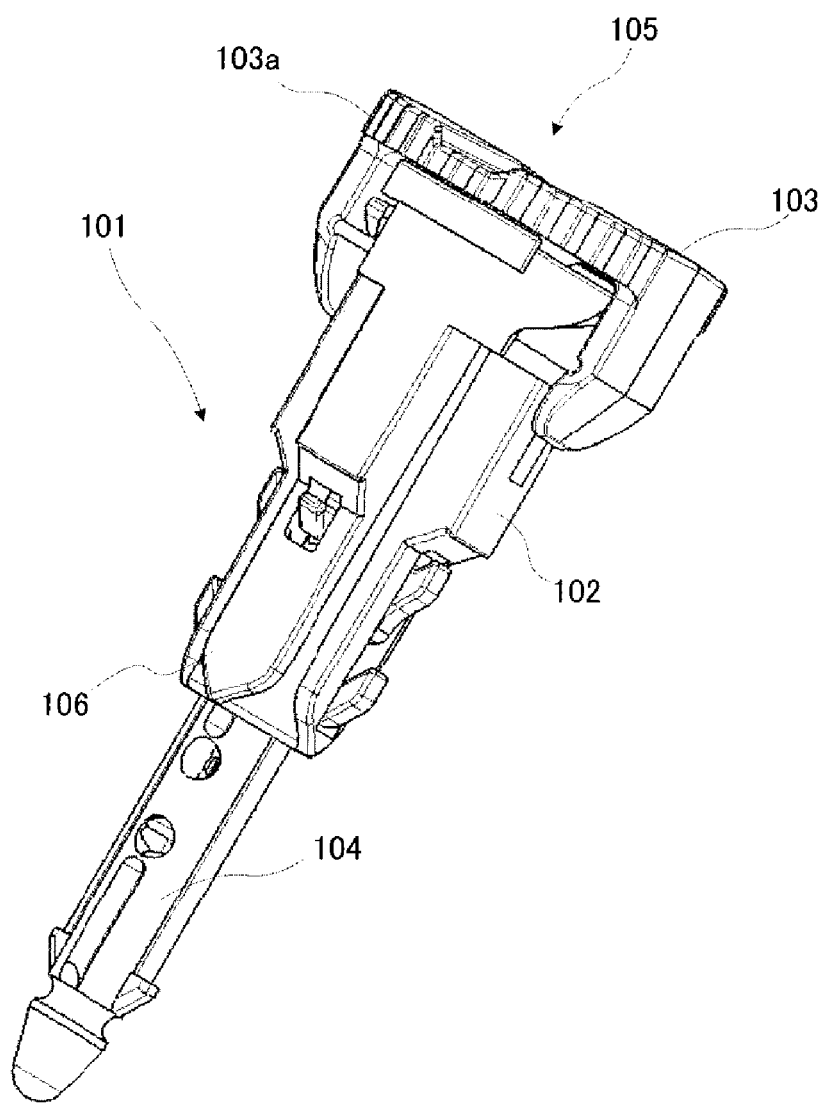
FIG. 1 is a perspective view showing an overall configuration of a puncture needle cartridge according to a first embodiment of the present invention.

FIG. 1 is a perspective view showing an overall configuration of a puncture needle cartridge according to a first embodiment of the present invention.

As shown in FIG. 1, a puncture needle cartridge 101 comprises a puncture needle holder 102 cylindrical in shape and a lancet 105 equipped with a protective cap 103 adapted to protect a puncture needle (not shown) installed on one end.

The lancet 105 comprises a lancet body 104 and the protective cap 103 adapted to cover a puncture needle in the lancet body 104. The lancet 105 is housed in a bore 106 of the cylindrical puncture needle holder 102.

Figure 2:
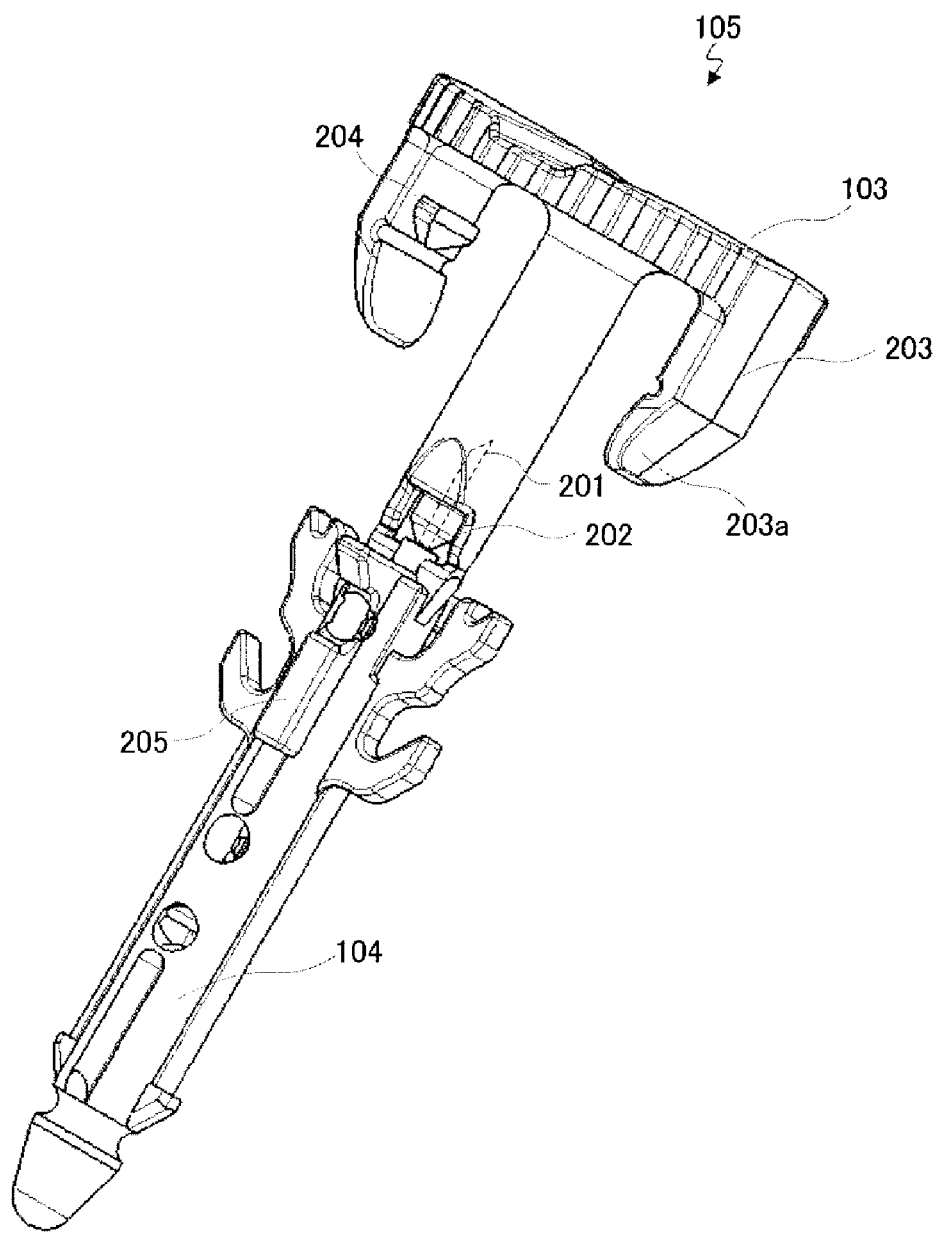
FIG. 2 is a perspective view of a lancet alone of the puncture needle cartridge according to the first embodiment before separation of a protective cap.

FIG. 2 is a perspective view of the lancet 105 before separation of the protective cap 103.

In FIG. 2, the lancet 105 comprises the lancet body 104 comprising a puncture needle 201, and the protective cap 103 adapted to protect the puncture needle 201.

The lancet body 104 and protective cap 103 are integrally formed of an elastic material such as polyethylene or other resin, and a tear-off portion 202 is provided therebetween to allow the protective cap 103 to be separated from the lancet body 104. Before use, the protective cap 103 is separated from the lancet body 104 at the tear-off portion 202, and one end of the contained puncture needle 201 is exposed from the lancet body 104. The protective cap 103 comprises raised walls 203, each of which has a claw 204 installed on the inner side of the raised walls 203. An inclined portion 203a which is inclined inward is installed in a tip portion of the raised wall 203 to prevent recapping. Also, the lancet body 104 has ribs 205 on side faces.

In this way, the puncture needle cartridge 101 comprises the puncture needle 201 adapted to puncture the skin, the lancet body 104 adapted to cover and protect part or all of a tip of the puncture needle 201, the puncture needle holder 102 configured to be cylindrical, placed on an outer circumferential surface of the lancet body 104 so as to allow the lancet body 104 to move in an axial direction of the puncture needle 201, and provided with an opening 102a (see FIG. 4 described later) through which the puncture needle 201 is allowed to protrude, and the protective cap 103 adapted to cover and protect the opening 102a (see FIG. 4) and configured to be separable from the puncture needle holder 102.

The protective cap 103 comprises a base 103a (see FIG. 1) adapted to cover the opening 102a (see FIG. 4) when the protective cap 103 is joined and a pair of the raised walls 203 which protrude from the base 103a toward the puncture needle holder 102 and whose tip portions are placed facing each other.

The inclined portions 203a located at the tips of the raised walls 203 and inclined inward (inclined toward the axis of the protective cap 103) pinch the puncture needle holder 102 when the protective cap 103 is joined to the puncture needle holder 102, and when the protective cap 103 is separated from the puncture needle holder 102, a space between the tips of the inclined portions 203a becomes smaller than the outside diameter of the puncture needle holder 102.

Figure 3:
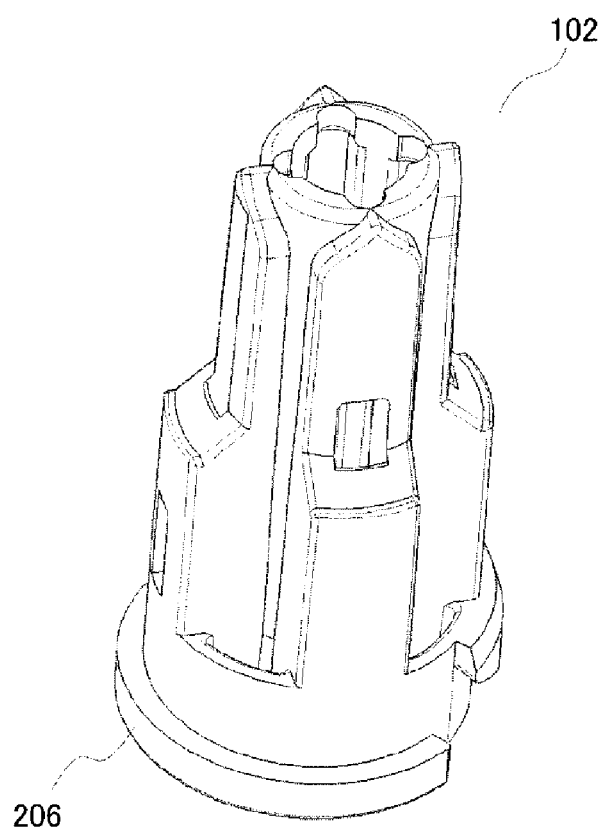
FIG. 3 is a perspective view of a puncture needle holder of the puncture needle cartridge according to the first embodiment when viewed obliquely from the front.
Figure 4:
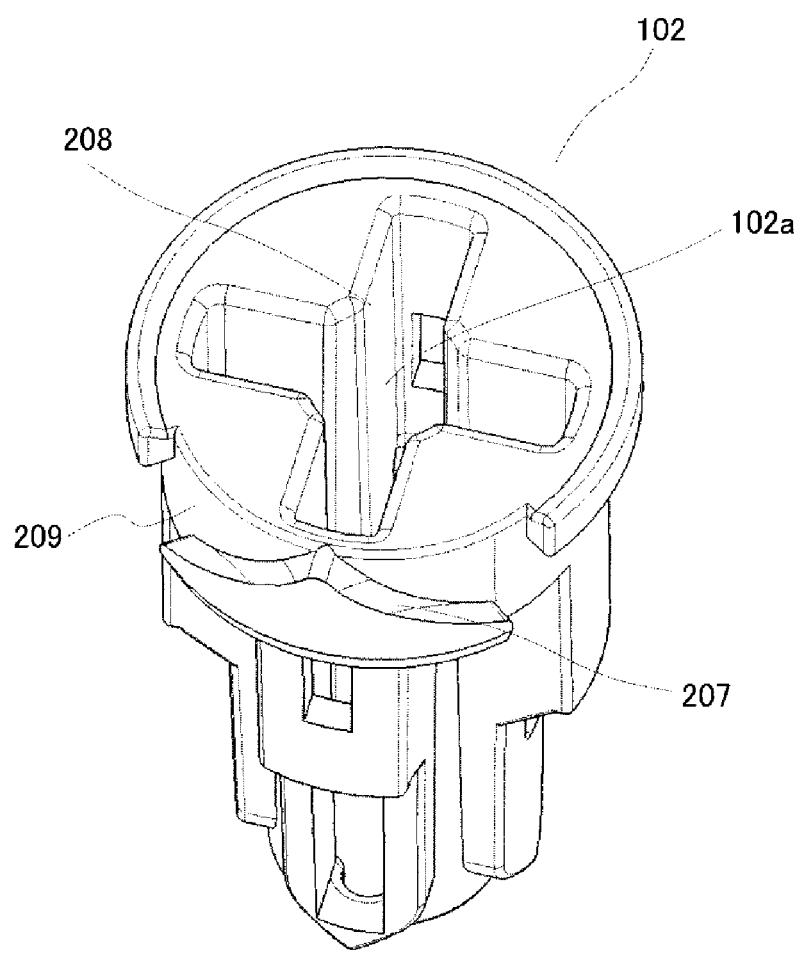
FIG. 4 is a perspective view of the puncture needle holder of the puncture needle cartridge according to the first embodiment when viewed obliquely from the rear.

FIGS. 3 and 4 are external views of the puncture needle holder 102, which is viewed obliquely from the front in FIG. 3, and obliquely from the rear in FIG. 4.

In FIGS. 3 and 4, the puncture needle holder 102 has a flange 206, which is engaged with the claws 204 inside the raised walls 203 of the protective cap 103.

A slope 207 is formed in the flange 206 to provide a guide portion. Furthermore, a cross slot 208 is formed in the puncture needle holder 102. The ribs 205 installed on the lancet body 104 are designed to fit in the cross slot 208, establishing relative axial position between the puncture needle holder 102 and the lancet 105 and thereby defining mutual position in an initial state. The flange 206 is positioned so as to engage with the claws 204 of the protective cap 103 in the initial state. Also, a recess 209 is provided so that the flange 206 will be disengaged from the claws 204 inside the raised walls 203 of the protective cap 103 when the protective cap 103 rotates a predetermined amount around an axis of the lancet body 104.

Next, regarding the puncture needle cartridge 101 configured as described above, a process from its installation on a puncture device 301 to its disposal will be described.

Figure 5:
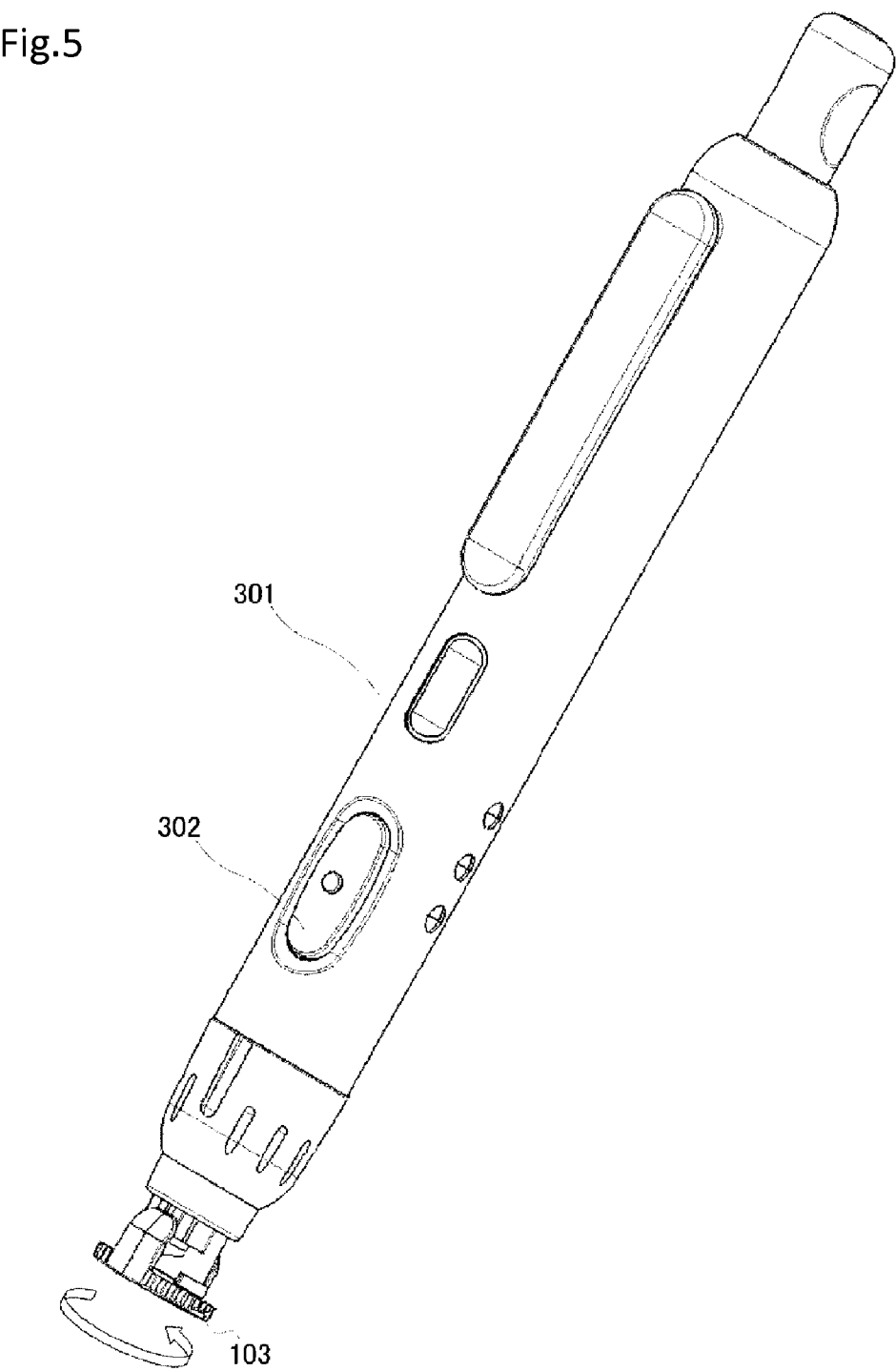
FIG. 5 is a perspective view showing the state where the puncture needle cartridge according to the first embodiment has been attached to a puncture device.
Figure 6:
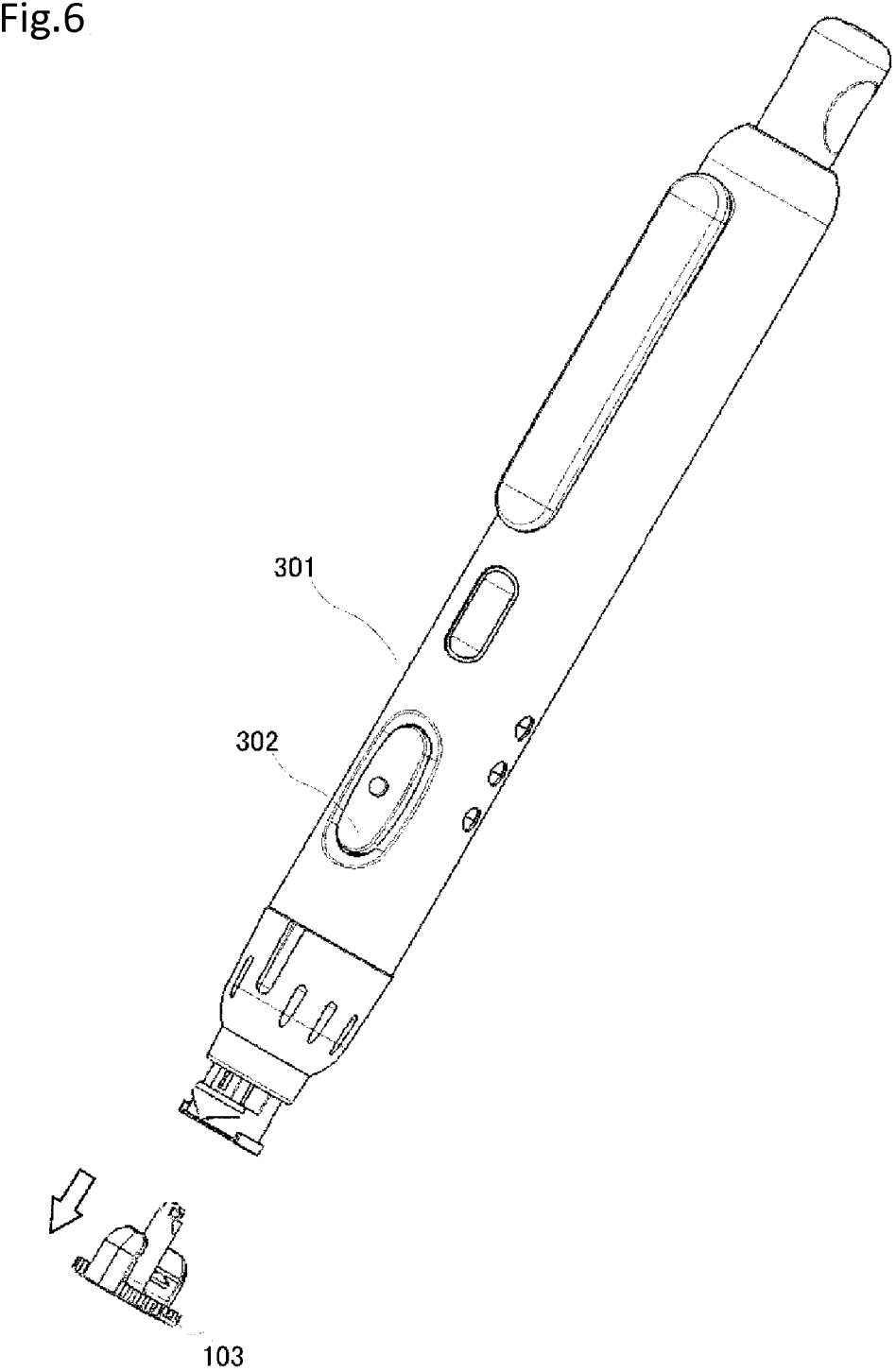
FIG. 6 is a perspective view showing the state where the protective cap has been separated from the puncture needle cartridge according to the first embodiment attached to the puncture device.
Figure 7:
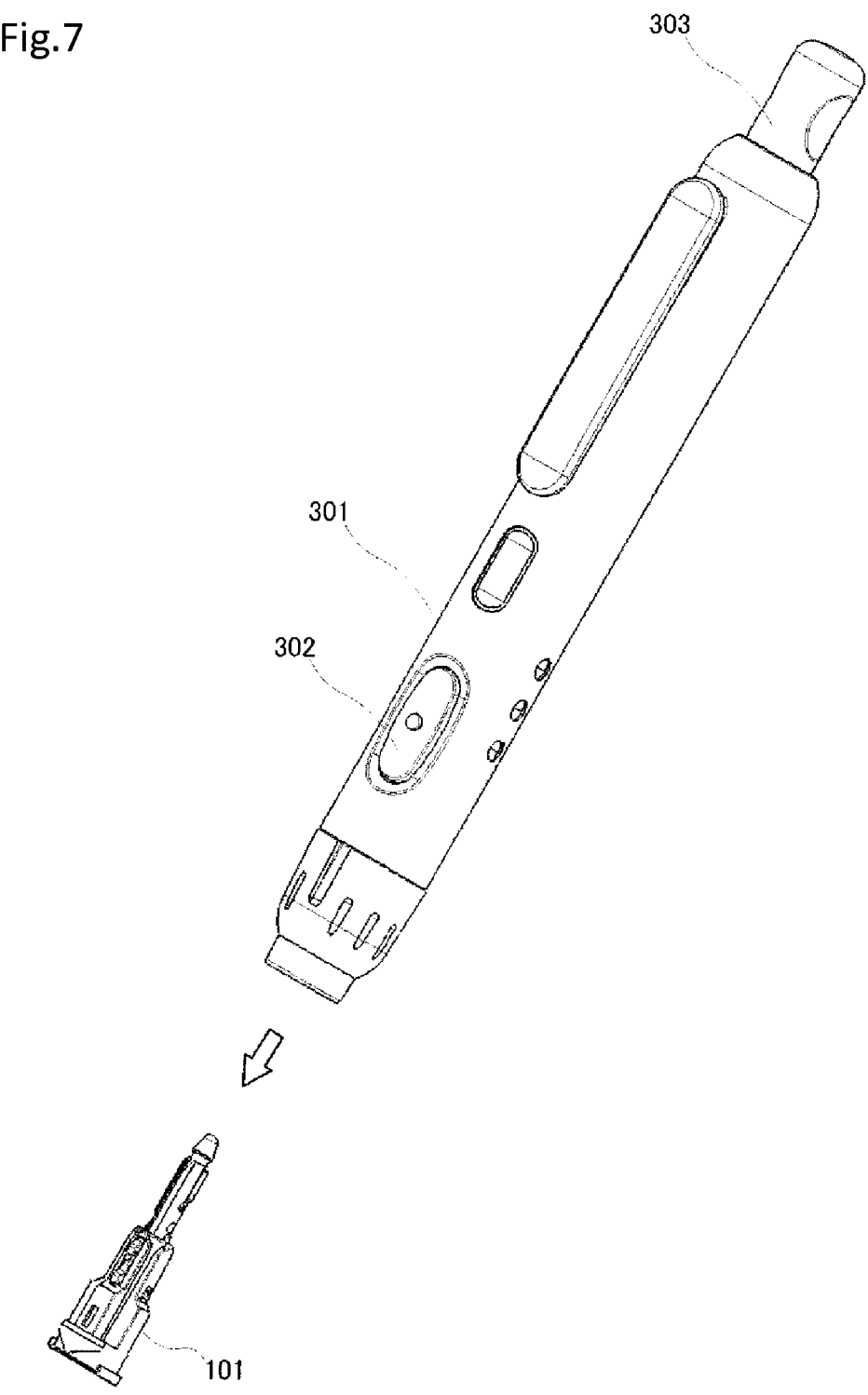
FIG. 7 is a perspective view showing the state where the puncture needle cartridge according to the first embodiment is disposed of after being used for puncture by being attached to the puncture device.

FIGS. 5 to 7 are perspective views showing installation, separation, and disposal of the puncture needle cartridge 101, respectively, with respect to the puncture device 301.

FIG. 5 shows the state where the puncture needle cartridge 101 has been attached to the puncture device 301.

By rotating the protective cap 103 around an axis of the puncture device 301 as indicated by a arrow in FIG. 5, the protective cap 103 can be separated from the lancet body 104 at the tear-off portion 202 (FIG. 2).

FIG. 6 shows the state where the protective cap 103 of the puncture needle cartridge 101 has been separated at the tear-off portion 202 (see FIG. 2) after the puncture needle cartridge 101 is attached to the puncture device 301. Consequently, part of the puncture needle 201 (see FIG. 2) which has been covered by the protective cap 103 is exposed from the lancet body 104, allowing the puncture device 301 to puncture the skin.

In this case, although exposed from the lancet body 104 of the lancet 105, the puncture needle 201 is kept behind an end of the puncture needle holder 102 fitted with the lancet 105, and is not exposed outside the puncture needle holder 102 unless a puncture button 302 or the like provided on the puncture device 301 is pressed. Thus, it is safe.

FIG. 7 shows disposal of the puncture needle cartridge 101.

After a puncture operation, when an ejection button 303 or the like provided on the puncture device 301 is pressed, the used puncture needle cartridge 101 is disposed of as shown in FIG. 7.

Next, a recapping prevention function and operation of the puncture needle cartridge 101 according to the present invention will be described.

The term "recapping" means attaching the protective cap 103 once separated to the lancet body 104 again. Recapping makes it difficult to visually tell a used puncture needle cartridge from an unused one, and consequently a used puncture needle cartridge could be attached to the puncture device 301 again by mistake.

The recapping prevention operation of the puncture needle cartridge 101 according to the present invention will be described with reference to FIGS. 8 to 11.

Figure 8:
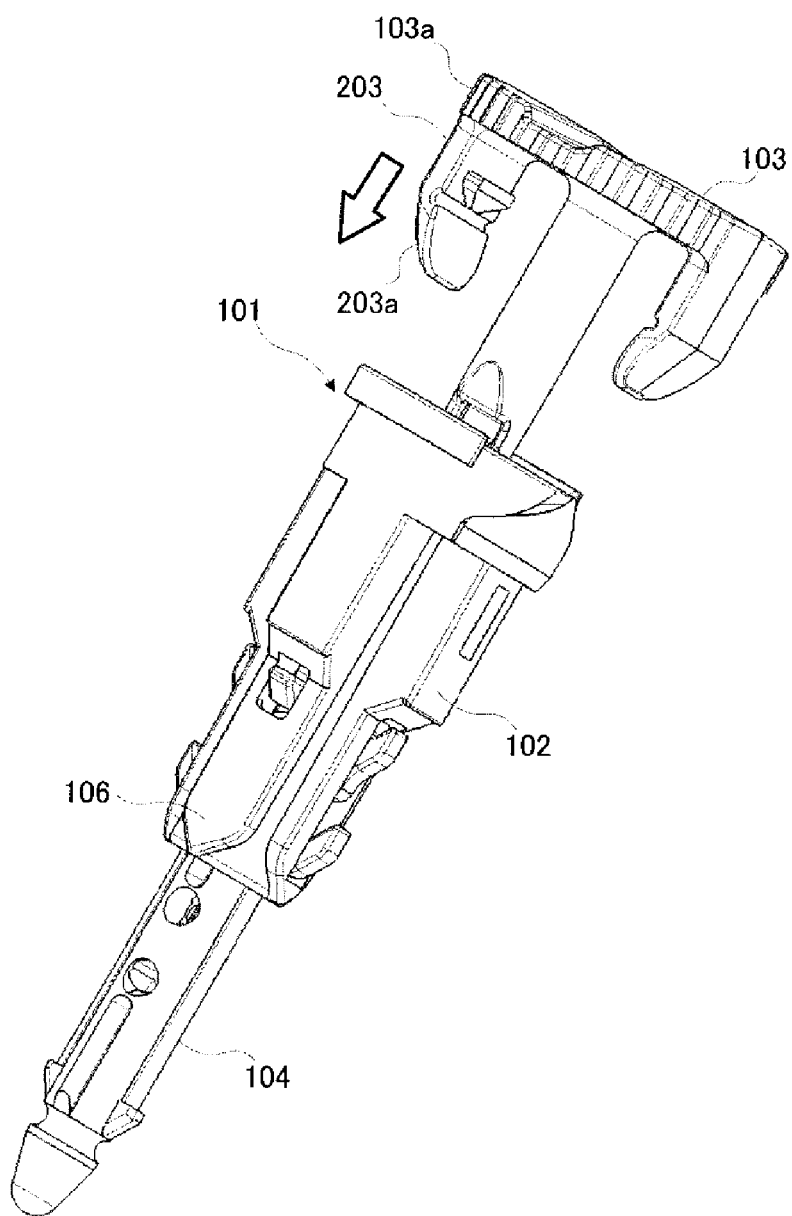
FIG. 8 is a diagram illustrating a recapping prevention operation of the puncture needle cartridge according to the first embodiment.
Figure 9:
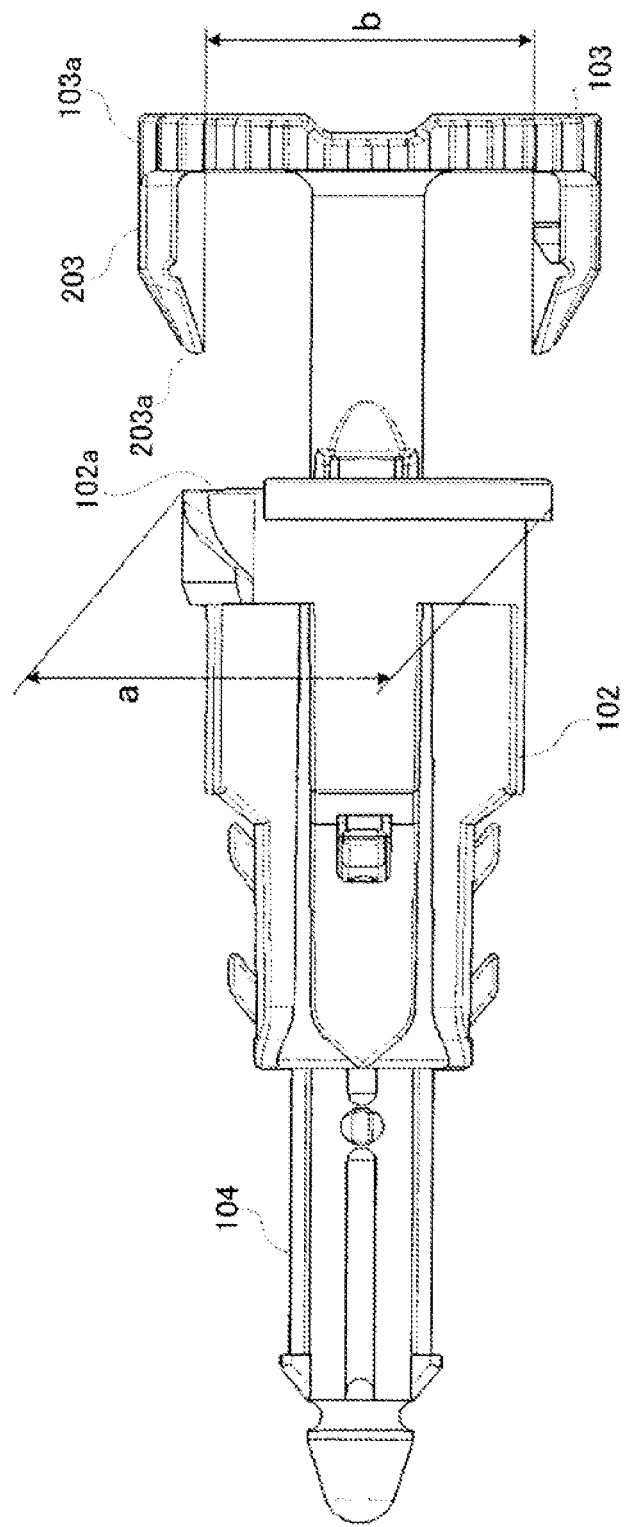
FIG. 9 is a diagram illustrating the recapping prevention operation of the puncture needle cartridge according to the first embodiment.
Figure 10:
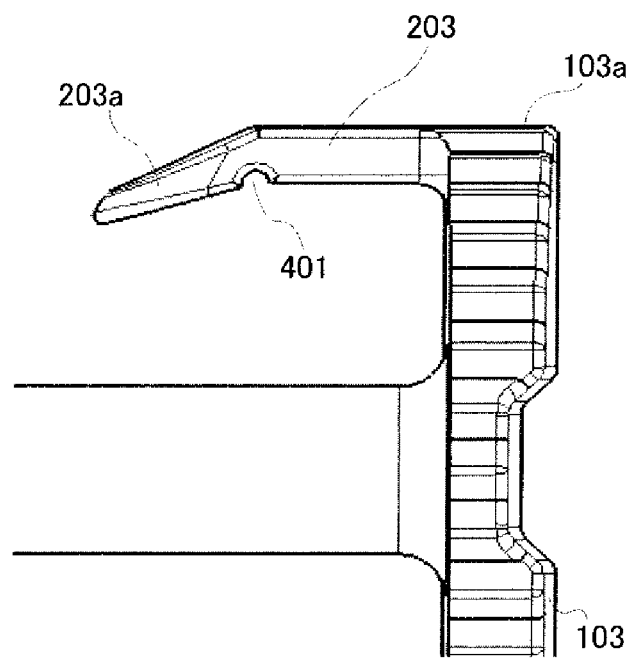
FIG. 10 is a diagram illustrating the recapping prevention operation of the puncture needle cartridge according to the first embodiment.
Figure 11:
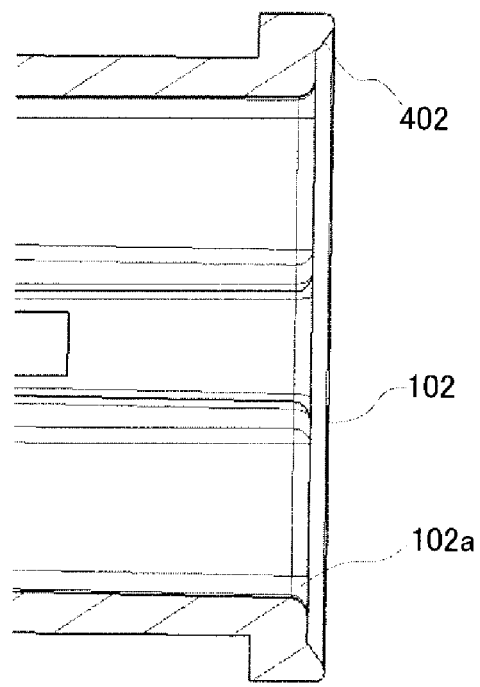
FIG. 11 is a diagram illustrating the recapping prevention operation of the puncture needle cartridge according to the first embodiment.

FIG. 8 is a perspective view showing the state where the puncture needle cartridge 101 is about to be recapped with the protective cap 103, FIG. 9 is a side view showing the state where the puncture needle cartridge 101 is about to be recapped with the protective cap 103, FIG. 10 is an enlarged view of principal parts of the protective cap 103, and FIG. 11 is an enlarged view of an end of the puncture needle holder 102.

FIG. 8 shows action that a used puncture needle cartridge 101 removed from the puncture device 301 is about to be recapped with the protective cap 103 once separated.

The protective cap 103 comprises the raised walls 203, which comprises the inclined portions 203a installed in tip portions and inclined inward (toward the center). The inclined portions 203a of the raised walls 203 are inclined inward, and the space (see size b) between the tip portions of the inclined portions 203a is smaller than the outside diameter size (see size a) of the puncture needle holder as shown in FIG. 9.

With this configuration, if there is an attempt to recap the used puncture needle cartridge 101 with the separated protective cap 103, the inclined portions 203a of the raised walls 203 engage with the puncture needle holder 102 by entering inside the end of the puncture needle holder 102, restraining the used puncture needle cartridge 101 from moving further inward in the puncture needle holder 102 and thereby preventing recapping.

Also, as shown in FIG. 10, a groove 401 is provided in a boundary portion between the raised wall 203 and the inclined portion 203a. The groove 401 makes it easier for the inclined portion 203a to incline inward when a force is applied in a direction of the axis.

Furthermore, as shown in FIG. 10, the interior angle formed by the raised wall 203 and inclined portion 203a is larger than 90 degrees and smaller than 180 degrees. The wall thickness of the inclined portion 203a is not larger than the wall thickness of the raised wall 203 and decreases toward the tip.

Furthermore, as shown in FIG. 11, a projection 402 for guiding purposes is provided on a tip surface of the puncture needle holder 102 to prevent the inclined portions 203a of the raised walls 203 from climbing over outer periphery of the puncture needle holder 102. Incidentally, the inner circumferential face of the guiding projection 402 may be tapered.

This allows the inclined portions 203a of the raised walls 203 provided on the protective cap 103 to enter inside the puncture needle holder 102 more reliably, improving the reliability of recapping prevention.

As described above in detail, according to the present embodiment, the puncture needle cartridge 101 comprises the puncture needle holder 102, configured to be cylindrical, placed on the outer circumferential surface of the lancet body 104 so as to allow the lancet body 104 to move in the axial direction of the puncture needle 201, and provided with the opening 102a through which the puncture needle 201 is allowed to protrude; and the protective cap 103 adapted to cover and protect the opening 102a and configured to be separable from the puncture needle holder 102. The protective cap 103 comprises the base 103a adapted to cover the opening 102a when the protective cap 103 is joined to the puncture needle holder 102 and the pair of raised walls 203 which protrude from the base 103a toward the puncture needle holder 102 and whose tip portions are placed facing each other. The inclined portions 203a located at the tips of the raised walls 203 and inclined inward pinch the puncture needle holder 102 when the protective cap 103 is joined to the puncture needle holder 102, and when the protective cap 103 is separated from the puncture needle holder 102, the space between the tip portions of the inclined portions 203a becomes smaller than the outside diameter of the puncture needle holder 102. That is, the inclined portions 203a of the raised walls 203 are inclined inward, and the space (see size b) between the tips of the inclined portions 203a is smaller than the outside diameter size (see size a) of the puncture needle holder as shown in FIG. 9.

With this configuration, if there is an attempt to recap the puncture needle cartridge 101 with the protective cap 103, the inclined portions 203a engage with the puncture needle holder 102 by entering inside the tip portion of the puncture needle holder 102, preventing recapping. Since this configuration reliably prevents a patient from recapping the puncture needle cartridge 101 with the protective cap 103 after puncturing, it is possible to determine at a glance whether the puncture needle cartridge 101 is a used item or an unused item based on whether the puncture needle cartridge 101 is capped or not. This prevents a used needle from being reused by mistake and thereby prevents a danger of infection accidents.

(Second Embodiment)

Figure 12:
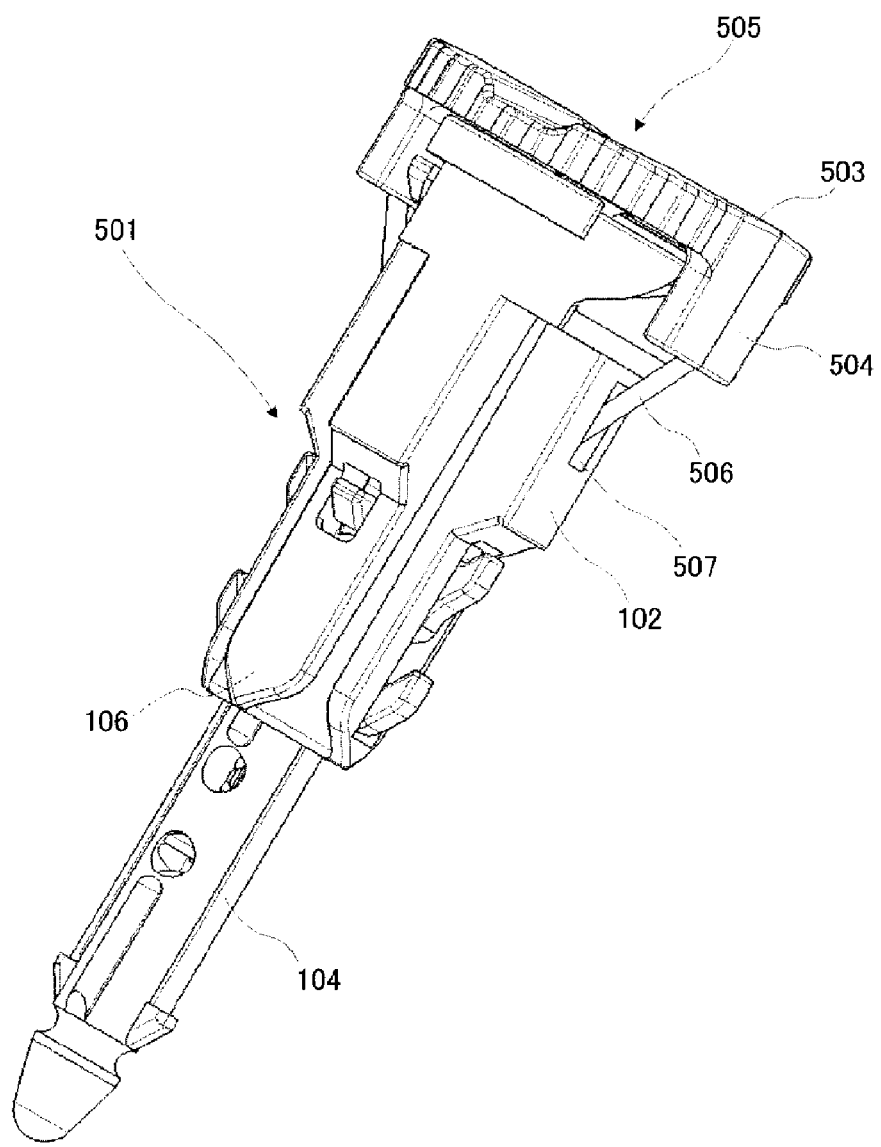
FIG. 12 is a perspective view showing an overall configuration of a puncture needle cartridge according to a second embodiment of the present invention.

FIG. 12 is a perspective view showing an overall configuration of a puncture needle cartridge according to a second embodiment of the present invention. In the description of the second embodiment, the same components as those in the first embodiment in FIGS. 1 and 2 are denoted by the same reference numerals as the corresponding components in the first embodiment, and redundant description thereof will be omitted.

In FIG. 12, a puncture needle cartridge 501 comprises a puncture needle holder 102 cylindrical in shape and a lancet 505 equipped with a protective cap 503 adapted to protect a puncture needle installed on one end.

The lancet 505 comprises a lancet body 104 and the protective cap 503 adapted to cover a puncture needle in the lancet body 104. The lancet 505 is housed in a bore 106 of the cylindrical puncture needle holder 102.

The lancet body 104 and protective cap 503 are integrally formed of an elastic material such as polyethylene or other resin, and a tear-off portion 603 (see FIG. 13 described later) is provided therebetween to allow the protective cap 503 to be separated from the lancet body 104. The protective cap 503 comprises two raised walls 504, each of which is provided with a boss 506 inclined inward to prevent recapping.

Also, the puncture needle holder 102 is provided with through-holes 507 to allow passage of the bosses 506.

According to the second embodiment, the raised walls 504 of the protective cap 503 are linked to the lancet body 104 via the two bosses 506. Roles of the two bosses 506 are to prevent recapping and assist resin inflow during molding of the lancet 505.

Figure 13:
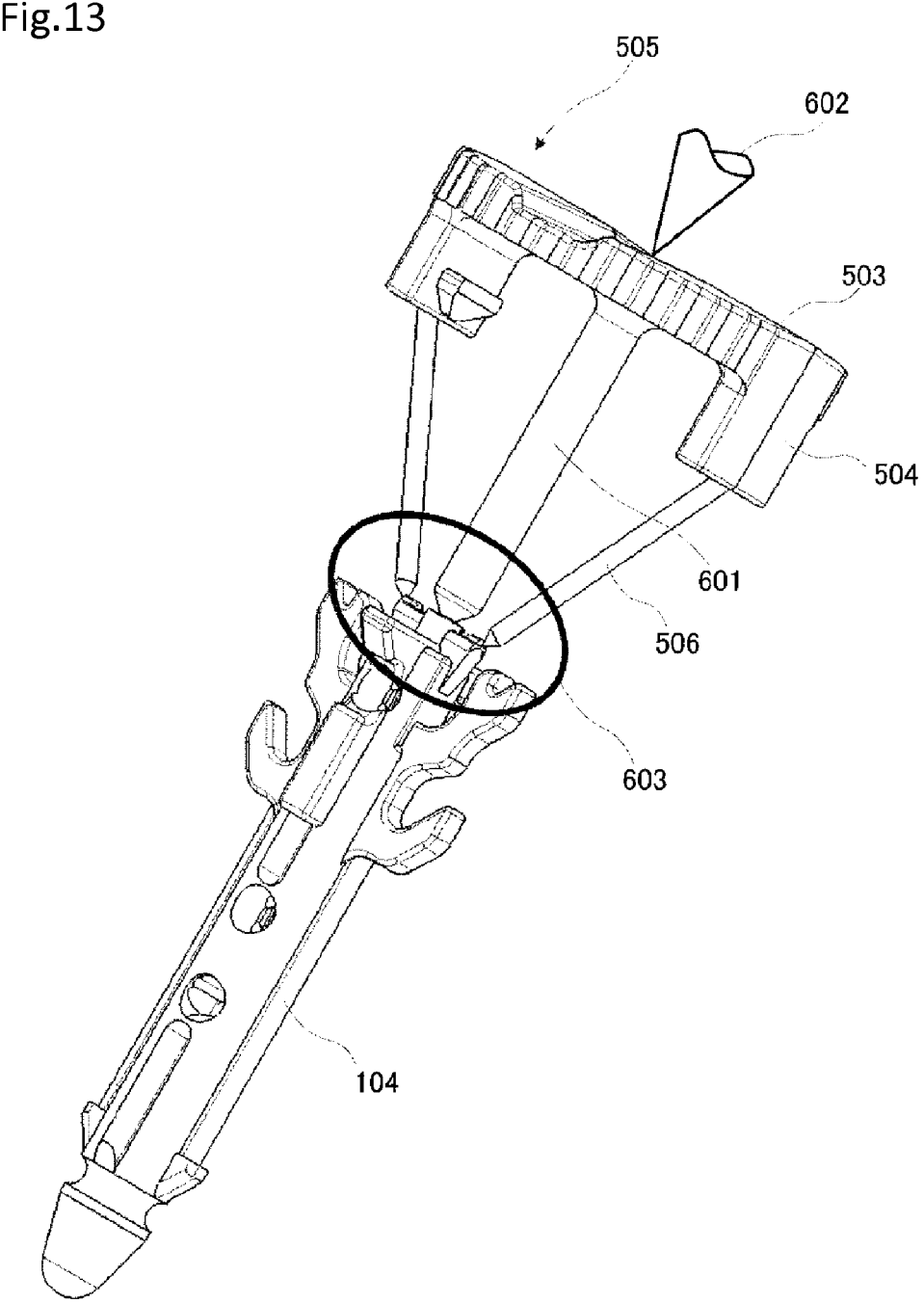
FIG. 13 is a perspective view of a lancet alone of the puncture needle cartridge according to the second embodiment.
Figure 14:
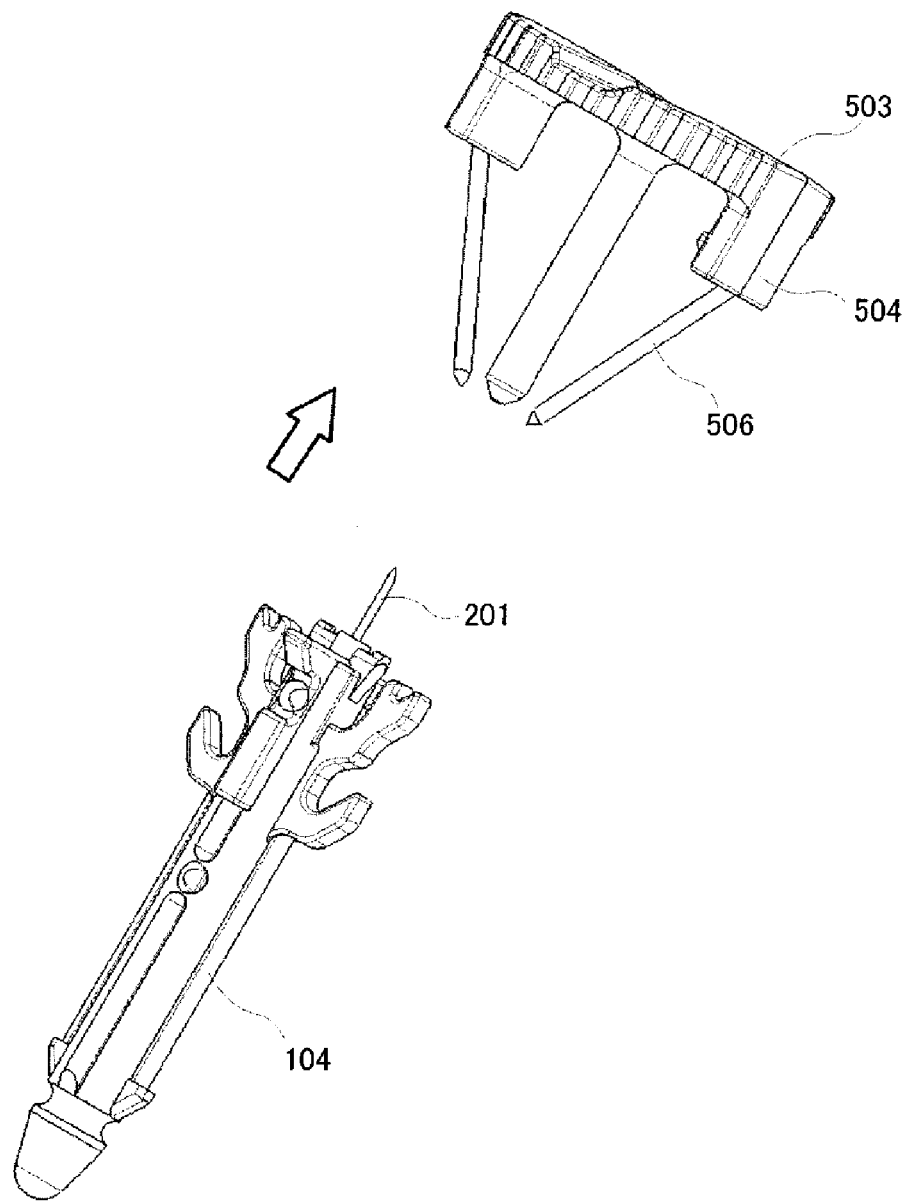
FIG. 14 is a diagram showing how a protective cap and bosses have been separated from a lancet body of the puncture needle cartridge according to the second embodiment.

FIG. 13 is an external perspective view of the lancet 505 alone before separation of the protective cap 503 and FIG. 14 is an external perspective view showing the state where the protective cap 503 has been separated from the lancet body 104. Incidentally, a gate 602 which serves as an input port for resin from a molding machine during molding of the lancet 505 is also shown in FIG. 13.

As shown in FIG. 13, to prevent recapping with the protective cap 503, diameter of a shaft 601 covering the puncture needle on the side of the protective cap 503 is designed to be smaller than diameter of the lancet body 104.

Position of the gate 602 during molding of the lancet is as shown in FIG. 13. During molding of the lancet, resin is inputted from the molding machine (not shown) via the gate 602.

When the diameter of the shaft 601 is reduced, that resin flow during molding will be impaired, which might result in defective molding (such as a short shot) of the lancet body 104. For the purpose of compensating for this, the raised walls 504 and lancet body 104 are linked together via the bosses 506 to secure a flow path for the resin during molding. Again, the tear-off portion 603 is provided between the lancet body 104 and the bosses 506 to allow the protective cap 503 to be twisted off at the tear-off portion 603.

FIG. 14 shows the protective cap 503 and lancet body 104 separated from each other at the tear-off portion 603.

The two bosses 506 provided on the protective cap 503 are separated together with the protective cap 503 at the tear-off portion 603.

Although two bosses 506 are provided in the second embodiment, the number of bosses 506 is not limited to two, and may be one or more than two. However, from the standpoint of recapping prevention effect, two or more is preferable.

Next, a recapping prevention operation of the puncture needle cartridge 501 will be described.

Figure 15:
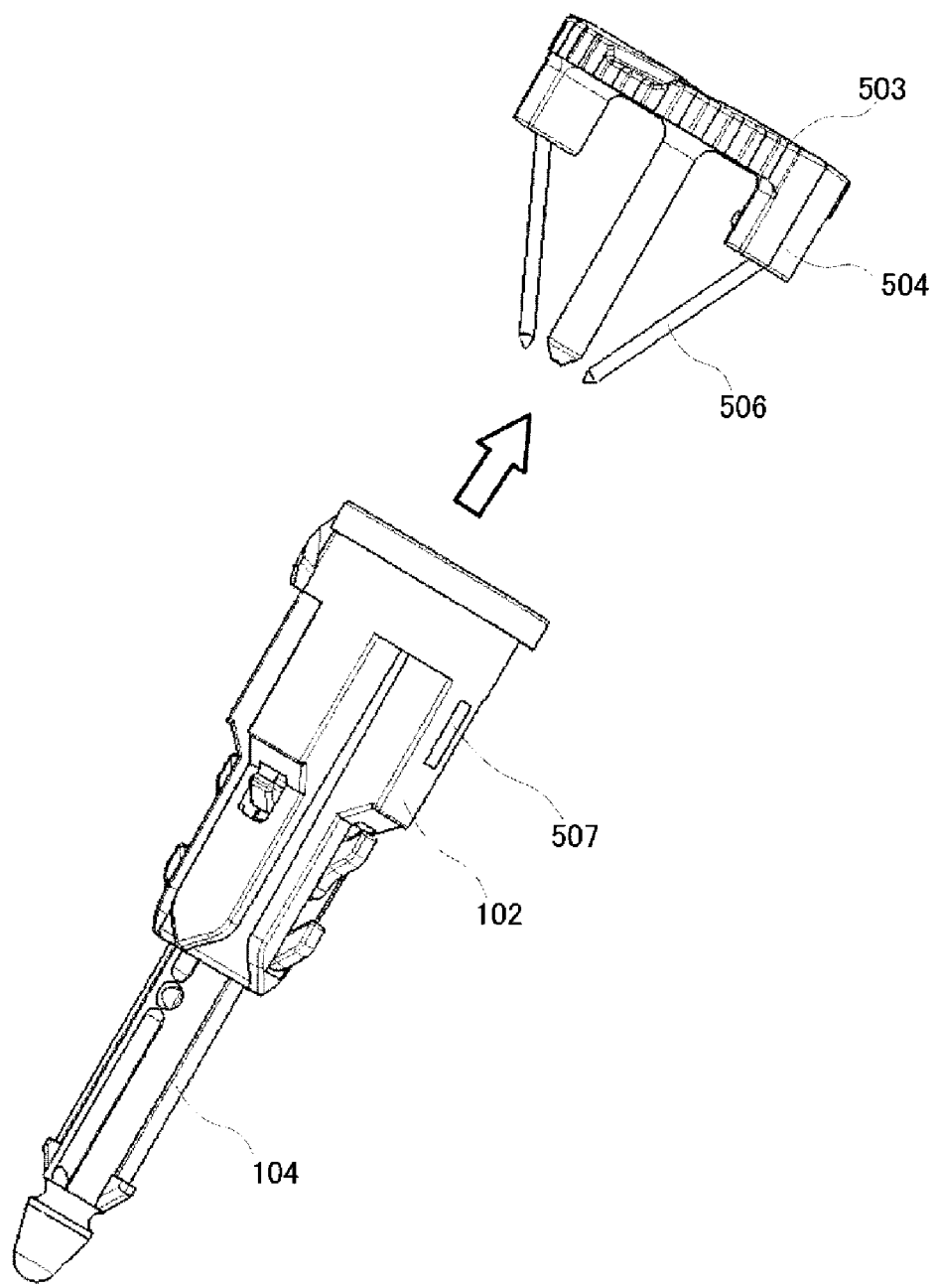
FIG. 15 is a diagram illustrating a recapping prevention operation of the puncture needle cartridge according to the second embodiment.
Figure 16:
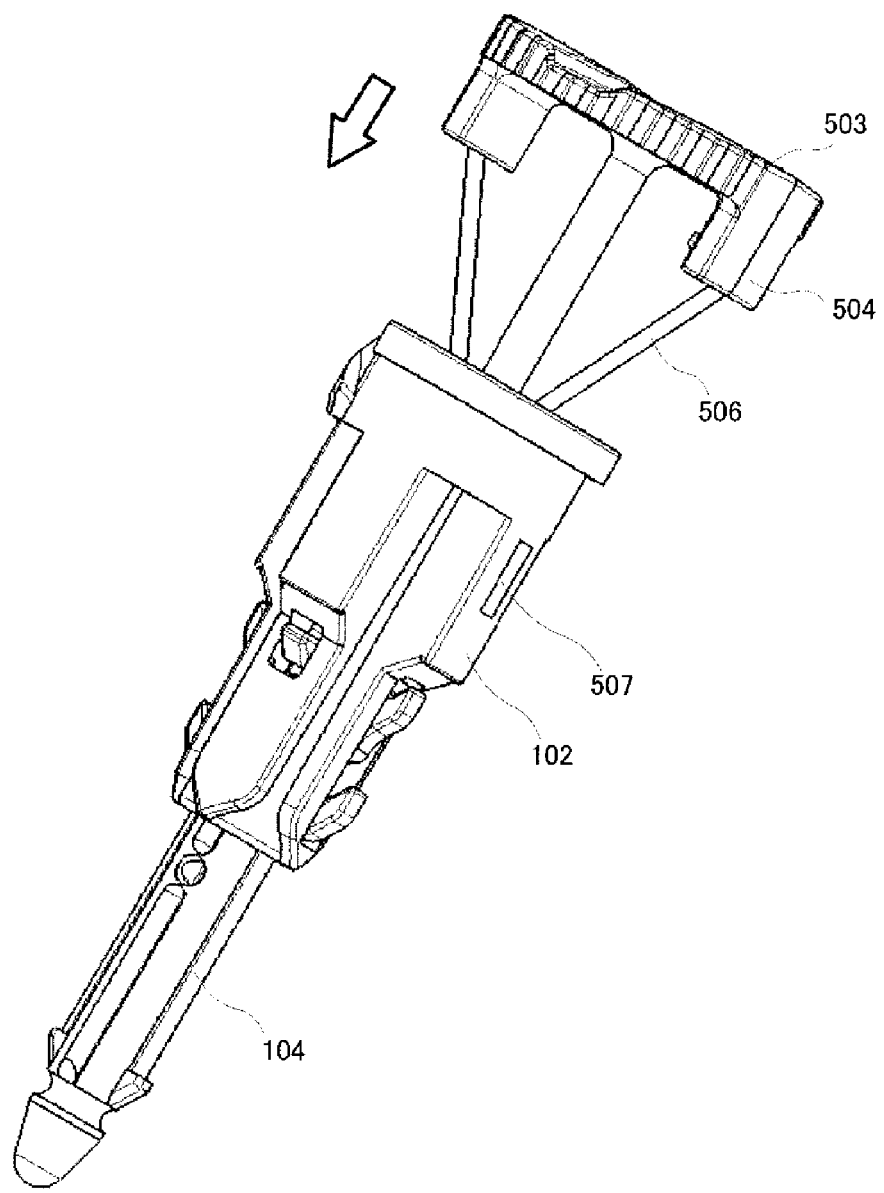
FIG. 16 is a diagram illustrating the recapping prevention operation of the puncture needle cartridge according to the second embodiment.

FIGS. 15 and 16 are diagrams illustrating a recapping prevention operation of the puncture needle cartridge 501, where FIG. 15 shows the puncture needle cartridge 501 with the protective cap 503 separated from the lancet body 104 and FIG. 16 shows the puncture needle cartridge 501 about to be recapped with the protective cap 503.

The lancet 505 incorporated in the puncture needle holder 102 (see FIG. 12) is attached to the puncture device 301 shown in FIG. 5.

When the protective cap 503 is twisted off, the tear-off portion 603 with three tear-off points is torn, separating the protective cap 503 at the tear-off portion 603 on the shaft 601 and causing the two bosses 506 to come off the through-holes 507 in the puncture needle holder 102 and thereby separate from the tear-off portion 603, as in the case of the first embodiment (see FIGS. 6 and 15).

Consequently, part of the puncture needle 201 (see FIG. 2) which has been covered by the protective cap 503 is exposed from the lancet body 104, allowing the puncture device 301 to puncture the skin.

In this case, although exposed from the lancet body 104 of the lancet 505, the puncture needle 201 is kept behind an end of the puncture needle holder 102 fitted with the lancet 505, and is not exposed outside the puncture needle holder 102 unless the puncture button 302 or the like provided on the puncture device 301 is pressed.

Let's assume that someone is about to recap the puncture needle cartridge 501 with the protective cap 503 after the puncture needle cartridge 501 is removed from the puncture device 301 and disposed of.

Even if someone attempts to put back the protective cap 503, it is difficult to stick the puncture needle 201 (see FIGS. 2 and 16) into the shaft 601, which has a small diameter. This makes it difficult to fixedly hold the protective cap 503 and thereby making recapping difficult. Furthermore, the two bosses 506, which are inclined inward in the direction of the shaft 601, are engaged with the opening 102a or cross slot 208 (see FIG. 4) of the puncture needle holder 102 and are unable to move further into the puncture needle holder 102, making it difficult to return the bosses 506 to the through-holes 507 of the puncture needle holder 102. For the two reasons just mentioned, the bosses 506 installed on the protective cap 503 engage with the puncture needle holder 102 without coordination. This prevents recapping.

In this way, in the puncture needle cartridge 501 according to the second embodiment, the protective cap 503 comprises the bosses 506 formed on an end portion of the raised walls 504 and the puncture needle holder 102 comprises the through-holes 507 adapted to allow passage of the bosses 506. With this configuration, if there is an attempt to recap the puncture needle cartridge 501 with the protective cap 503, the bosses 506 engage with an end portion of the puncture needle holder 102 without coordination and thereby prevent recapping. In addition, if the bosses 506 are pulled out of the through-holes 507 of the puncture needle holder 102 once, it is a fairly difficult task to put the bosses 506 back into the through-holes 507 of the puncture needle holder 102. This makes it possible to reliably prevent a patient from recapping the puncture needle cartridge 501 with the protective cap 503 after puncturing, making it possible to prevent the puncture needle cartridge containing a used needle from being reused by mistake and thereby prevents a danger of infection accidents, as in the case of the first embodiment.

(Third Embodiment)

Figure 17:
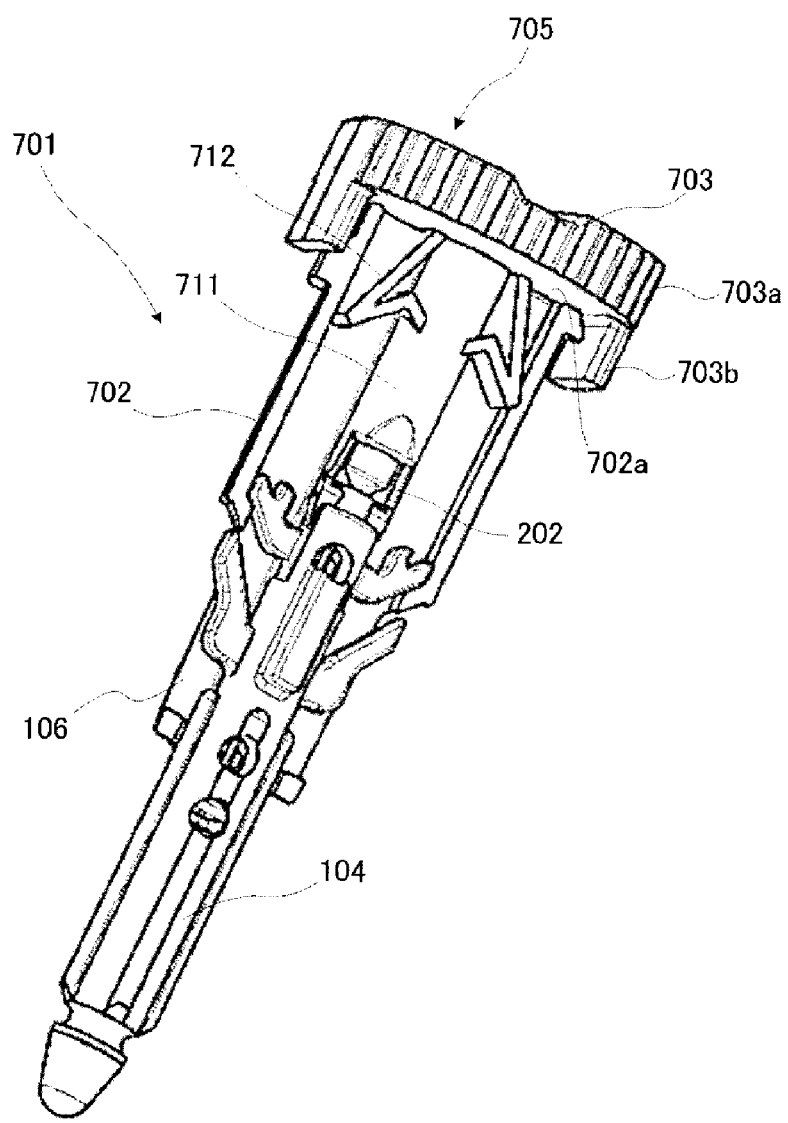
FIG. 17 is a partially cutaway perspective view showing a puncture needle cartridge according to a third embodiment of the present invention.
Figure 18:
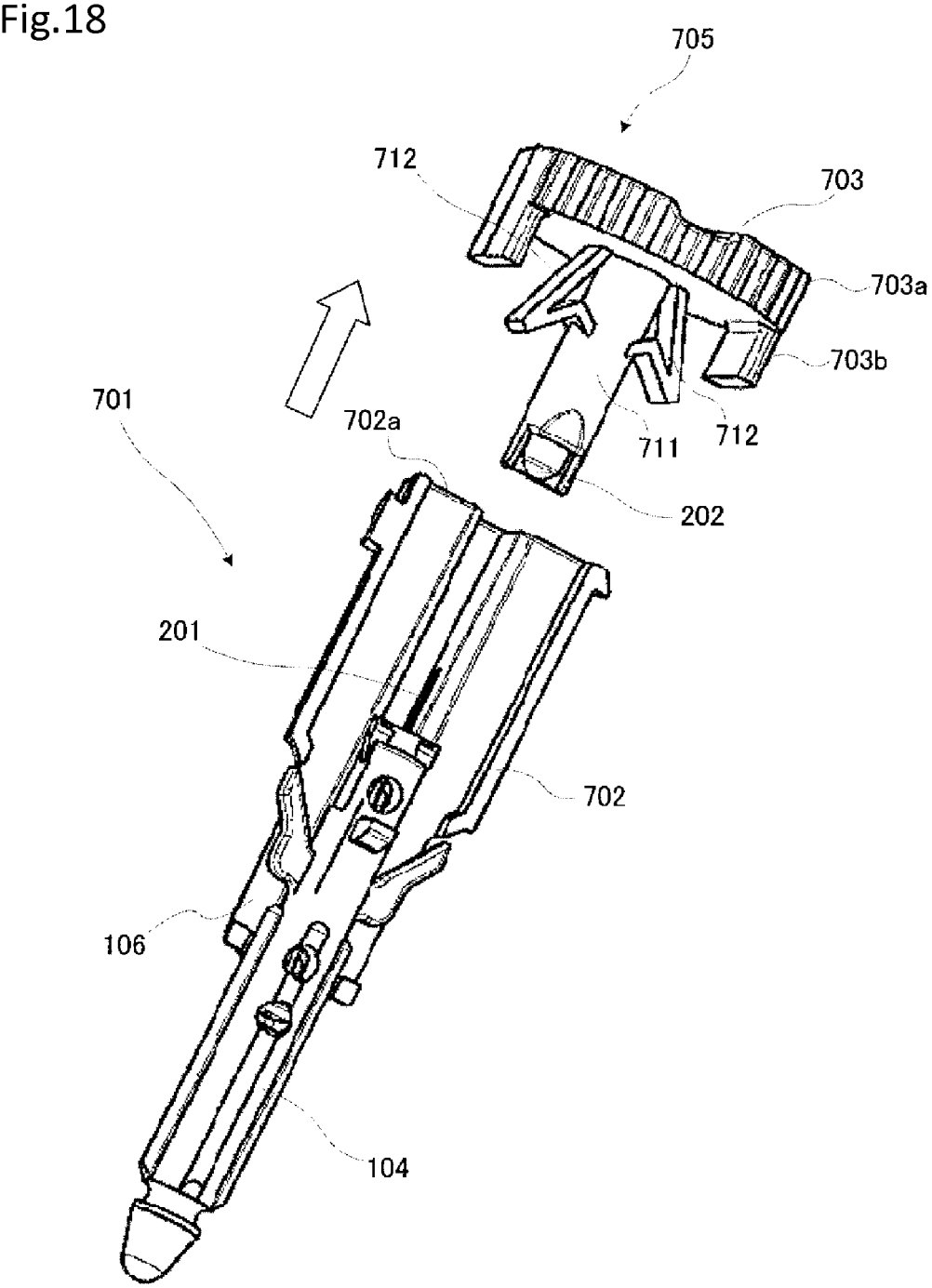
FIG. 18 is a perspective view showing how a protective cap has been separated from the puncture needle cartridge according to the third embodiment.
Figure 19:
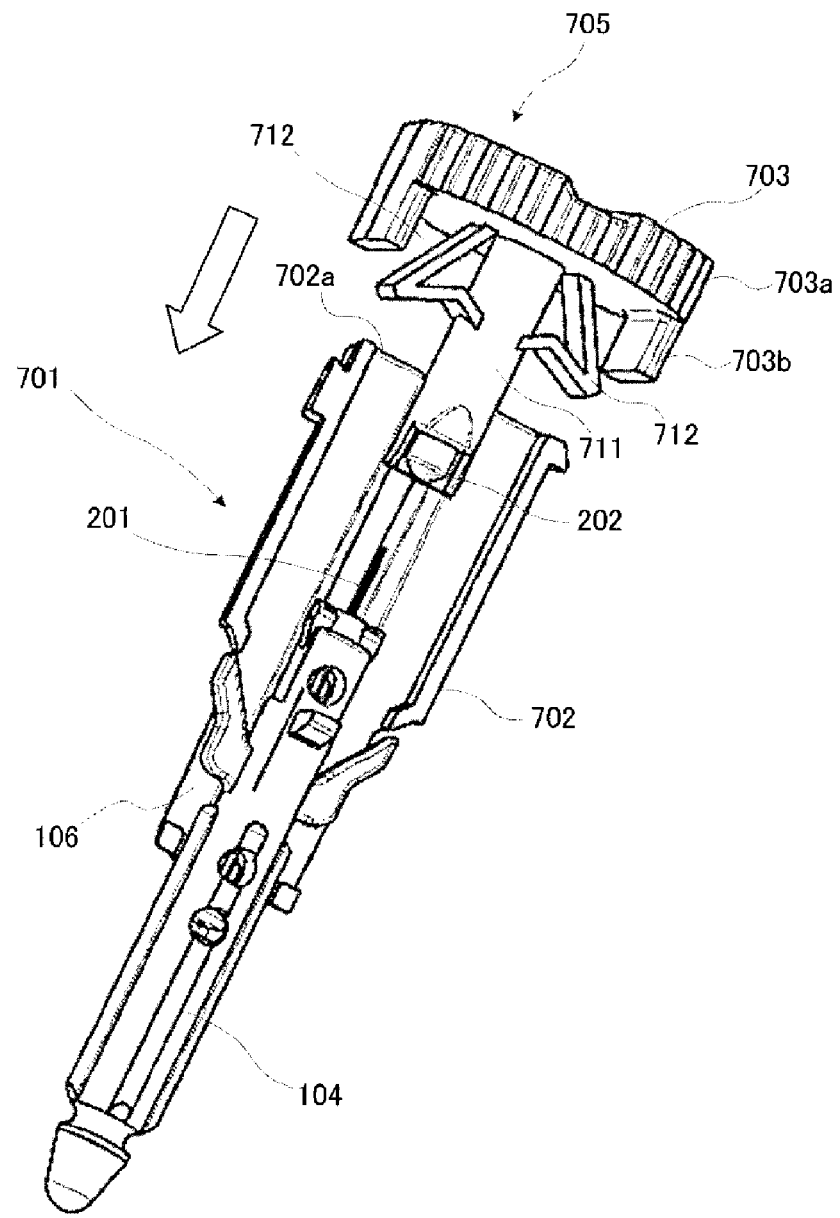
FIG. 19 is a diagram showing the state where the puncture needle cartridge according to the third embodiment is about to be recapped with the protective cap for the puncture needle cartridge.

FIGS. 17 to 19 are partially cutaway perspective views showing a puncture needle cartridge according to a third embodiment of the present invention, where FIG. 17 is a perspective view of a lancet 705 before a protective cap 703 is separated, and FIGS. 18 and 19 are perspective views showing the state where the protective cap 703 has been separated. In the description of the third embodiment, the same components as those in the first embodiment in FIGS. 1 and 2 are denoted by the same reference numerals as the corresponding components in the first embodiment, and redundant description thereof will be omitted.

As shown in FIG. 17, a puncture needle cartridge 701 comprises a puncture needle holder 702 cylindrical in shape and the lancet 705 equipped with the protective cap 703 adapted to protect a puncture needle 201 (see FIG. 18) installed on one end.

The lancet 705 comprises a lancet body 104 and the protective cap 703 adapted to cover the puncture needle 201 (see FIG. 18) in the lancet body 104. The lancet 705 is housed in a bore 106 of the cylindrical puncture needle holder 702.

The puncture needle holder 702 is placed on an outer circumferential surface of the lancet body 104 so as to allow the lancet body 104 to move in an axial direction of the puncture needle 201 and provided with an opening 702a through which the puncture needle 201 is allowed to protrude.

The protective cap 703 is adapted to cover and protect the opening 702a in the puncture needle holder 702 and configured to be separable from the puncture needle holder 702.

The protective cap 703 comprises a base 703a adapted to cover the opening 702a when the protective cap 703 is joined, and raised walls 703b which protrude from the base 703a toward the puncture needle holder 702 by being placed facing each other. Also, the protective cap 703 comprises a shaft 711 protruding from the base 703a toward the opening 702a, and a pair of arms 712 mounted on the shaft 711 and adapted to abut an inner circumferential surface of the opening 702a in the puncture needle holder 702 by spreading in the opening 702a.

The arms 712 are claw portions mounted on the shaft 711 and made of an elastic material. Space between tips of the arms is larger than the inside diameter of the opening 702a in the puncture needle holder 702, and is reduced by elastic deformation when the tips of the arms are housed in the opening 702a.

Next, a recapping prevention operation of the puncture needle cartridge 701 will be described.

FIGS. 18 and 19 are diagrams illustrating a recapping prevention operation of the puncture needle cartridge 701, where FIG. 18 shows the puncture needle cartridge 701 with the protective cap 703 separated, and FIG. 19 shows the puncture needle cartridge 701 about to be recapped with the protective cap 703.

As shown in FIG. 17, the lancet 705 incorporated into the puncture needle holder 702 is attached to the puncture device 301 shown in FIG. 5.

As shown in FIG. 18, when the protective cap 703 is twisted off, the tear-off portion 202 is torn, separating the protective cap 703 from the shaft 711.

Consequently, part of the puncture needle 201 which has been covered by the protective cap 703 is exposed from the lancet body 104, allowing the puncture device 301 (see FIG. 5) to puncture the skin.

As shown in FIG. 19, if there is an attempt to recap the puncture needle cartridge 701 with the protective cap 703, since the arms 712 mounted on the shaft 711 and made of an elastic material have been widened in the outer circumferential direction of the shaft 711, the spread tips of the arms 712 abut the opening 702a in the puncture needle holder 702, keeping the arms 712 from moving further into the puncture needle holder 702 and thereby making recapping difficult. This prevents recapping.

According to the present embodiment, the arms 712 are mounted on the shaft 711 protruding from the base 703a of the protective cap 703 toward the opening 702a in the puncture needle holder 702. Thus, the present embodiment further provides the following advantages. (1) The arms 712, whose stroke resulting from elastic deformation is restrained by the shaft 711, are hard to deform elastically and thus effectively prevent recapping. (2) Also, the arms 712 can be installed in any desired locations on the shaft 711. For example, the arms 712 can be installed in such locations as to be able to reliably abut the opening 702a in the puncture needle holder 702. Also, the present embodiment provides the advantage of being able to readily increase the space between the tips of the arms 712 compared to an outer dimension of the puncture needle cartridge 701.

(Fourth Embodiment)

Figure 20:
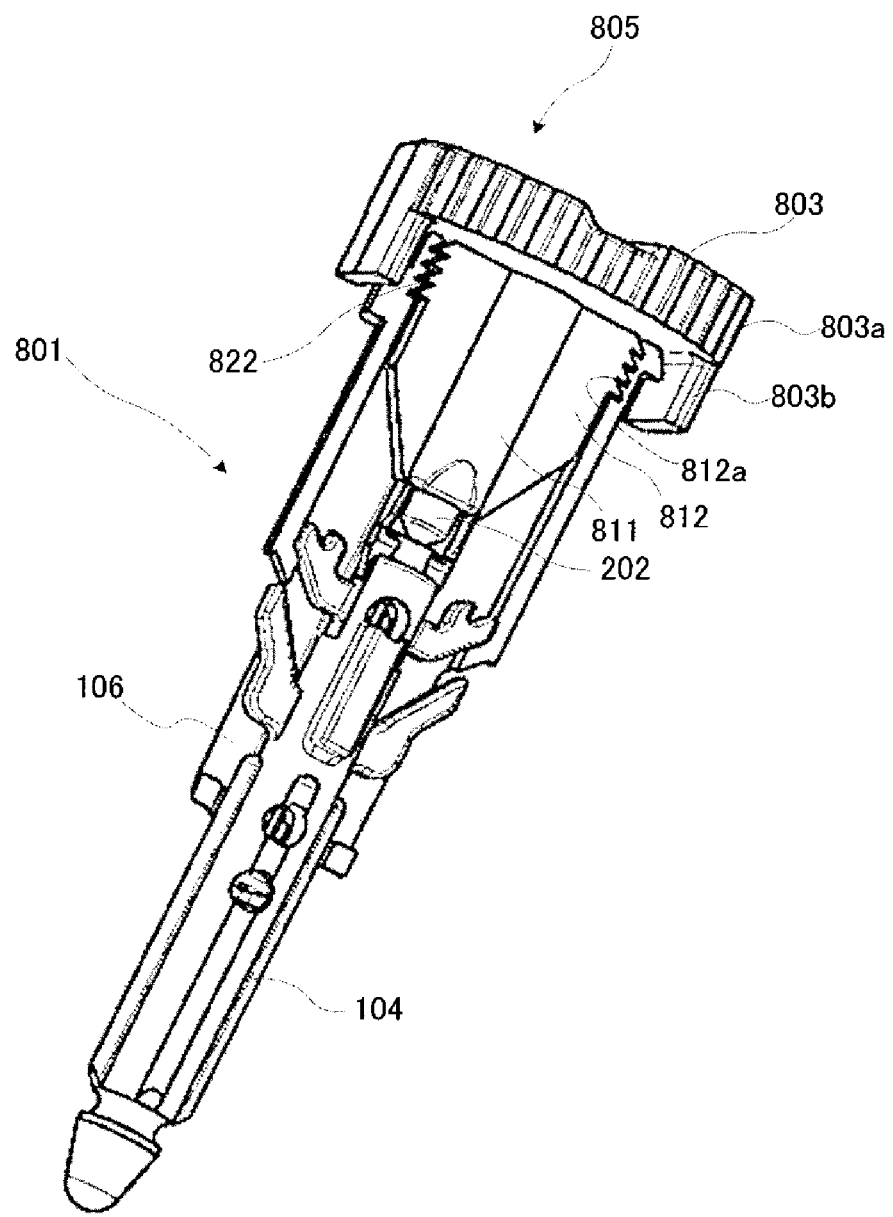
FIG. 20 is a partially cutaway perspective view showing a puncture needle cartridge according to a fourth embodiment of the present invention.
Figure 21:
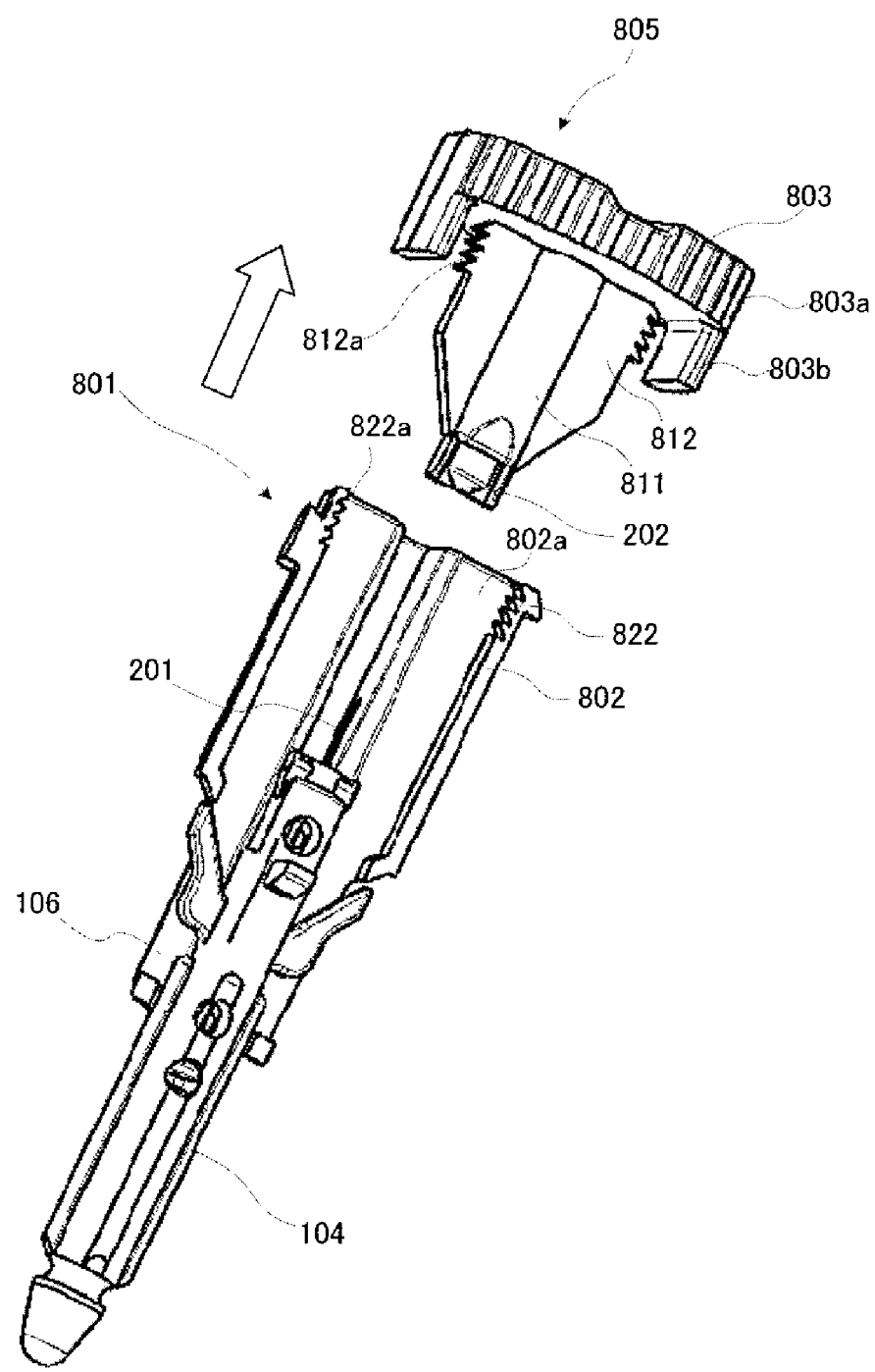
FIG. 21 is a perspective view showing how a protective cap has been separated from the puncture needle cartridge according to the fourth embodiment.
Figure 22:
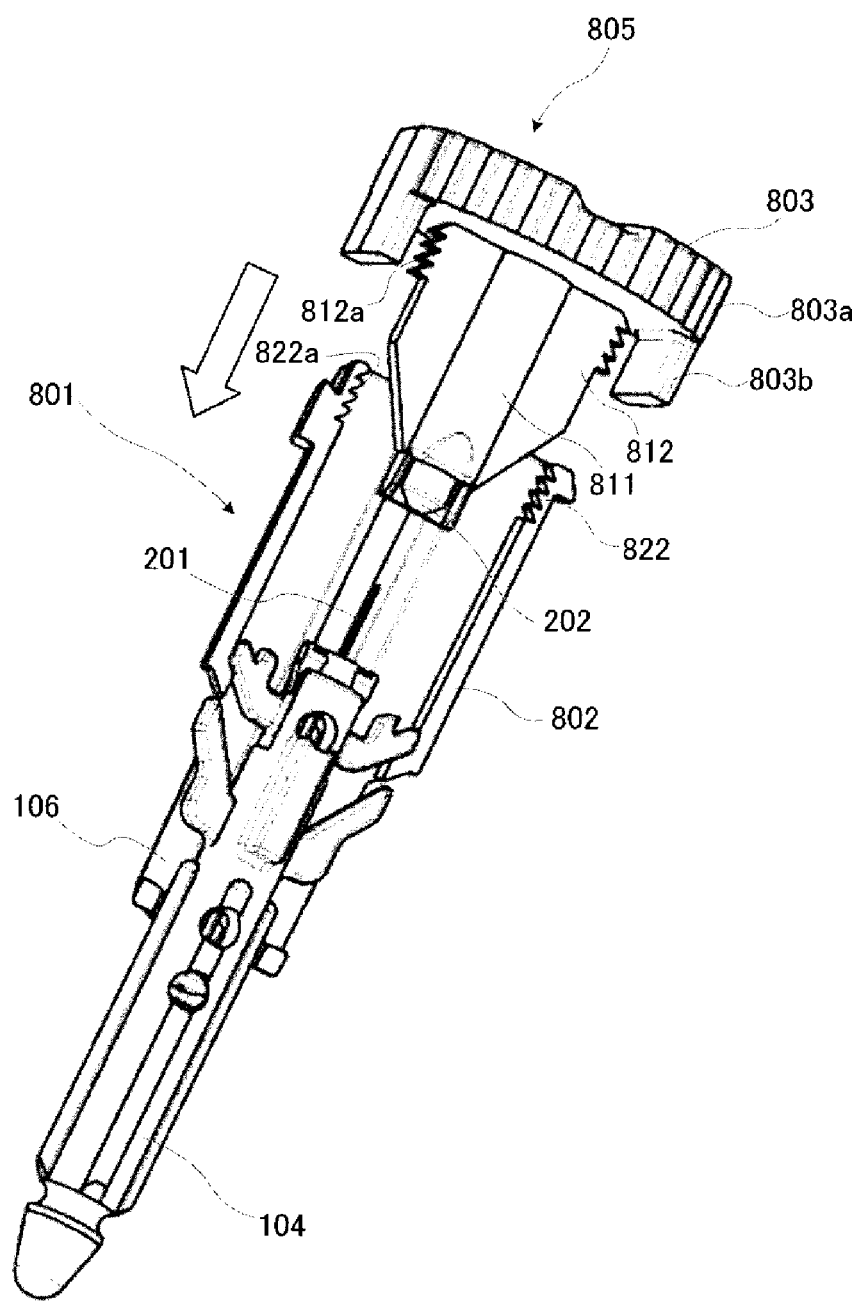
FIG. 22 is a perspective view showing the state where the puncture needle cartridge according to the fourth embodiment is about to be recapped with the protective cap for the puncture needle cartridge.

FIGS. 20 to 22 are partially cutaway perspective views showing a puncture needle cartridge according to a fourth embodiment of the present invention, where FIG. 20 is a perspective view of a lancet 805 before a protective cap 803 is separated, and FIGS. 21 and 22 are perspective views showing the state where the protective cap 803 has been separated. In the description of the fourth embodiment, the same components as those in the first embodiment in FIGS. 1 and 2 are denoted by the same reference numerals as the corresponding components in the first embodiment, and redundant description thereof will be omitted.

As shown in FIG. 20, a puncture needle cartridge 801 comprises a puncture needle holder 802 cylindrical in shape and the lancet 805 equipped with the protective cap 803 adapted to protect a puncture needle 201 (see FIG. 21) installed on one end.

The lancet 805 comprises a lancet body 104 and the protective cap 803 adapted to cover the puncture needle 201 (see FIG. 21) in the lancet body 104. The lancet 805 is housed in a bore 106 of the cylindrical puncture needle holder 802.

The puncture needle holder 802 is placed on an outer circumferential surface of the lancet body 104 so as to allow the lancet body 104 to move in an axial direction of the puncture needle 201 and provided with an opening 802a through which the puncture needle 201 is allowed to protrude as well as with a first engaging part 822 formed on an inner circumferential surface of the opening 802a and adapted to engage with a second engaging part 812 (described later).

The protective cap 803 is adapted to cover and protect the opening 802a and configured to be separable from the puncture needle holder 802.

The protective cap 803 comprises a base 803a adapted to cover the opening 802a when the protective cap 803 is joined, and raised walls 803b which protrude from the base 803a toward the puncture needle holder 802 by being placed facing each other. Also, the protective cap 803 comprises a shaft 811 protruding from the base 803a toward the opening 802a, and the second engaging part 812 formed on an outer circumferential surface of the shaft 811 and adapted to engage with the first engaging part 822.

The first engaging part 822 and second engaging part 812 separably engage with each other by elastic deformation in response to an action tending to separate the protective cap 803 from the lancet body 104 and comprise jagged surfaces 822a and 812a adapted to disable engagement in response to a recapping action tending to attach the protective cap 803 to the lancet body 104. The jagged surfaces 822a and 812a are shaped like a saw blades in cross section.

Next, a recapping prevention operation of the puncture needle cartridge 801 will be described.

As shown in FIG. 20, the lancet 805 incorporated in the puncture needle holder 802 as the puncture needle cartridge 801 is attached to the puncture device 301 shown in FIG. 5.

As shown in FIG. 21, when the protective cap 803 is twisted off, the tear-off portion 202 is torn, separating the protective cap 803 from the shaft 811.

The protective cap 803 is engaged with the puncture needle holder 802 via the first engaging part 822 and second engaging part 812. The first engaging part 822 and second engaging part 812 comprise the respective jagged surfaces 822a and 812a which can be separated in a removal direction of the protective cap 803 (direction of an arrow in FIG. 21). In response to an action tending to separate the protective cap 803 from the lancet body 104, the first engaging part 822 and second engaging part 812 elastically deform so as to slide along the respective jagged surfaces 822a and 812a, causing the protective cap 803 to be removed from the puncture needle holder 802.

Consequently, part of the puncture needle 201 which has been covered by the protective cap 803 is exposed from the lancet body 104, allowing the puncture device 301 (see FIG. 5) to puncture the skin.

As shown in FIG. 22, if there is an attempt to recap the puncture needle cartridge 801 with the protective cap 803, the second engaging part 812 formed on the outer circumferential surface of the shaft 811 and the first engaging part 822 formed on the inner circumferential surface of the opening 802a of the puncture needle holder 802 abut each other. However, in response to a recapping action tending to attach the protective cap 803 to the lancet body 104, the respective jagged surfaces 822a and 812a of the first engaging part 822 and second engaging part 812 act as edges (edges perpendicular to the shaft 811) which disable engagement. The abutment between the edges disables the protective cap 803 from engaging with the puncture needle cartridge 801 and thereby prevents recapping.

Incidentally, although in the present embodiment, the first engaging part 822 and second engaging part 812 comprise the jagged surfaces 822a and 812a configured as described above, the jagged surfaces may have any other geometry. That is, any geometry may be used as long as the first engaging part 822 and second engaging part 812 can disable engagement or make engagement difficult. For example, the edges may be oriented at an angle other than 90 degrees with respect to the direction of the shaft 811 instead of edges perpendicular to the shaft 811 direction, and the jagged surfaces 822a and 812a may be curved surfaces.

Although the present invention has been described with reference to preferred embodiments, the description is only illustrative of the present invention and is not to be viewed as limiting the scope of the present invention.

Although the term "puncture needle cartridge" has been used in the above embodiments for the convenience of explanation, needless to say, the term "puncture device," "puncture tool," "puncture apparatus," or the like may be used alternatively.

Also, components of the puncture needle cartridge including, for example, the type of cartridge, number of cartridges, and connection method may be selected as desired.

The entire disclosure of Japanese Patent Application No. 2008-262981 filed in Japan on Oct. 9, 2008 including the description, drawings, and abstract is incorporated herein by reference in its entirety.

The puncture needle cartridge according to the present invention is useful as a disposable puncture needle cartridge which comprises a replacement puncture needle for a puncture device used to take blood, and a puncture needle holder adapted to movably house the replacement puncture needle and configured to be replaceable together with the puncture needle.

The invention claimed is:

1. A puncture needle cartridge comprising:
a puncture needle configured to puncture skin;
a lancet body configured to cover and protect part or all of a tip of the puncture needle;
a cylindrical puncture needle holder disposed on an outer circumferential surface of the lancet body so as to enable the lancet body to move in an axial direction of the puncture needle, and having an opening through which the puncture needle is capable of protruding; and
a protective cap configured to cover and protect the opening and configured to be separable from the puncture needle holder,
wherein the protective cap comprises a base configured to cover the opening when the protective cap is joined to the puncture needle holder, a shaft protruding from the base toward the opening, and arms mounted on the shaft and configured to abut an inner circumferential surface of the opening in the puncture needle holder by spreading in the opening, and
space between tips of the arms is larger than an inside diameter of the opening in the puncture needle holder, and is reduced by elastic deformation when the arms are housed in the opening.

2. The puncture needle cartridge according to claim 1, wherein the arms are made of an elastic material.

3. The puncture needle cartridge according to claim 1, wherein the arms are installed in any desired locations on the shaft.

4. The puncture needle cartridge according to claim 1, wherein the protective cap and the shaft are connected via tear-off portion so that the protective cap and the shaft are separated when the tear-off portion is torn.

5. A puncture device configured to puncture skin using a needle, the device comprising:
a puncture button configured to puncture the skin with a needle,
wherein the puncture needle cartridge according to claim 1 is detachably attached to the puncture device, and
the puncture device punctures the skin using the attached puncture needle cartridge when the puncture button is pressed.

6. The puncture device according to claim 5, further comprising an ejection button configured to dispose of the puncture needle cartridge.

\* \* \* \* \*